March 6, 1956
R. C. NOTCUTT
Plant Pat. 1,457
RHUS COTINUS PLANT
Filed April 25, 1955
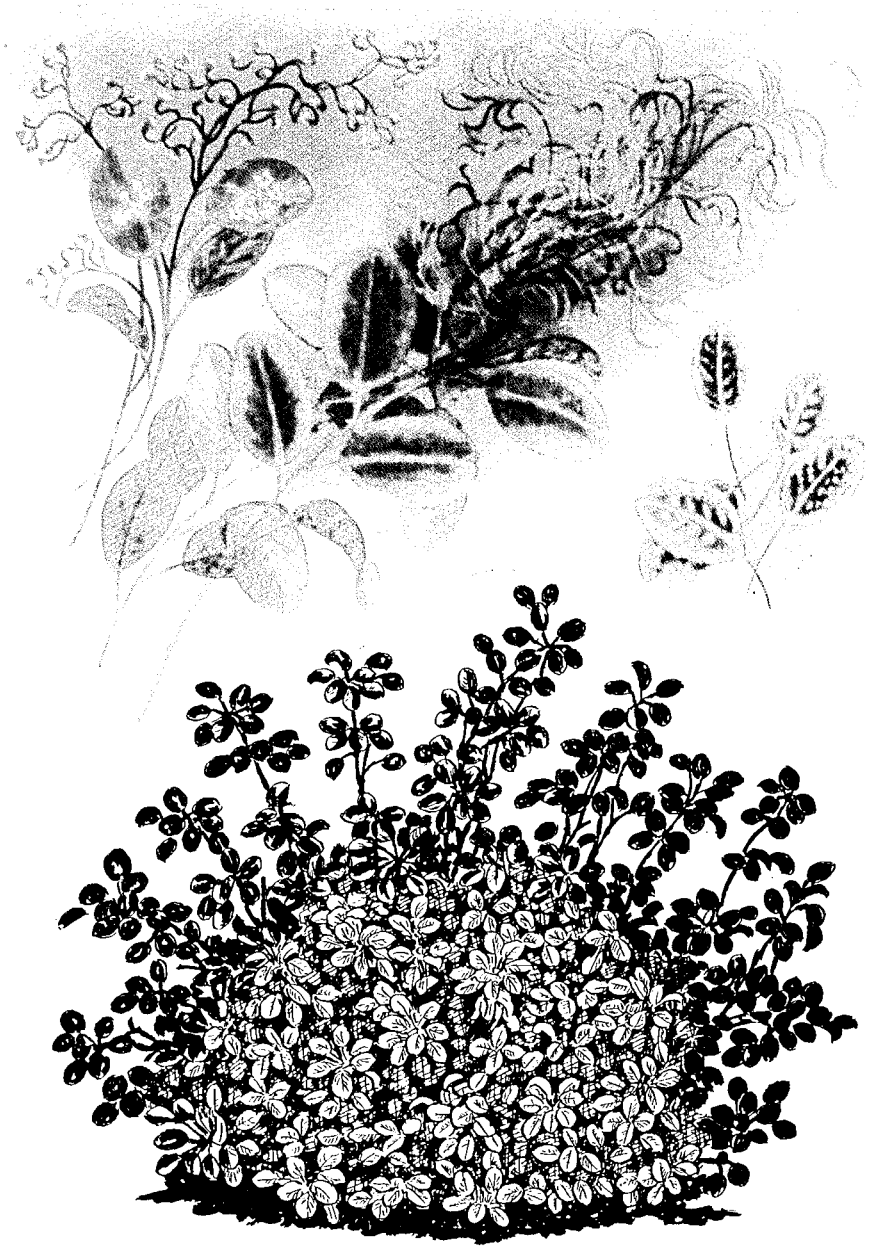
WITNESS
Addison J. Avery
INVENTOR
Roger Crompton Notcutt, deceased,
by Maud H. Notcutt, Executrix
by John H. Rhomard,
ATTY.

United States Patent Office

Plant Pat. 1,457

Patented Mar. 6, 1956

1,457

RHUS COTINUS PLANT

Roger Crompton Notcutt, deceased, late of Woodbridge, England, by Maud H. Notcutt, executrix, Woodbridge, England, assignor to John J. Grullemans, Cleveland, Ohio Application April 25, 1955, Serial No. 503,843

1 Claim. (Cl. 47—59)

This invention relates to a new and distinct variety of Rhus Cotinus plant and particularly to a Rhus Cotinus *Foliis purpureis.*

The new variety is illustrated in the drawings, in which:

The upper left hand view illustrates a typical branch with leaves and blossoms;

The upper central view illustrates some of the leaf and flower stalks of the plant as they appear later in the growing season than those illustrated in the upper left hand view; and The upper right hand view illustrates a number of typical leaves showing the characteristic patches or spots of mildew which occur on the upper surface of the leaves later in the season; and The pen and ink sketch at the bottom of the sheet is a front elevation of the plant as a whole, showing its general overall configuration.

The new variety is a chance seedling discovered by the applicant growing in a cultivated nursery bed in Woodbridge, Suffolk, England.

The parents are unknown.

The new variety was asexually reproduced by layering by the late Roger Crompton Notcutt, at Woodbridge, Suffolk, England.

The root system of the plant is a fibrous mass of average size for Rhus Cotinus plants.

The plant is somewhat shallow rooted with the roots having a lateral spread about equal to the upper exposed plant. The resistance of the roots to both wetness and drought is good. The roots do not appear to be bothered by diseases and insects. They have good winter resistance when unprotected, having withstood severe frosts in Suffolk, England. The root appears to do well in any ordinary soil.

The plant is a hearty woody shrub. The exposed part of the plant is relatively bushy and spreading, being somewhat rounded at the top. A typical eight year old plant is about five feet to six feet high with a spread of seven feet to eight feet. The general contour of the exposed plant is wide and regular, as indicated in the pen and ink sketch in the drawing.

The exposed part of the plant withstands low temperatures well when unprotected and withstands both drought and wet seasons. It prefers for best growth moderate or normally drained soil with moderate sunshine and a southern exposure. It grows well in almost all soils except very heavy clays.

The main stalks are upright and much branched. They are relatively stiff for a Rhus Cotinus plant and are adequate to support the foliage well.

In the remainder of the description, the references to color plates are to the plates of "A Dictionary of Color" by A. Maerz and M. Rea Paul, First Edition, 1930, except where otherwise noted.

The stalks generally are a Peony R+, comparable to Plate 6–J–6, the older growths being somewhat more brownish.

The main stalks have a relatively smooth textured surface and grow singly from the roots. The branches are alternately arranged and have about the same color and surface texture as the main stalks. They are generally long and curving, and are quite flexible, but adequate enough to support the bloom and foliage.

The foliage is somewhat open, the leaves being alternately arranged and of average quantity.

The top surfaces of the new leaves are of purple ranging in color from Plate 4–I–5 to Plate 45–I–4. The under-surfaces are a Mignon Green, comparable to Plate 21–J–6, with purplish shading along the veins.

The upper surfaces of the old leaves range from Amaryllis, comparable to Plate 5–I–5, to Old Mauve, comparable to Plate 46–I–5, and Pansy Purple, comparable to Plate 54–L–8, and quite often more than one, or all, of these colors appear on a single leaf surface.

The leaves are of a medium size, ranging in length from about 2" to 2½" and in width from 1¼" to 1½". They are generally ovate with an entire margin. The leaves are comparatively thin with waxy upper faces and glabrous under-faces.

The leaf stems are Peony R+, comparable to Plate 6–J–6. Their surfaces are smooth and they are of medium strength, being about 1½" in length.

The flowers are rather small and inconspicuous, being yellow, comparable to Plate 10–K–2. However, the plant produces at the ends of the branches large masses of purplish-grey hair-like sterile inflorescences, ranging in color from Plate 51–A–1 to Plate 53–A–3 and having the appearance of smoke from a distance. They first appear after the plant has a well established root system and persist on the plant for several months. They are borne on branches which are not pruned annually.

These sterile inflorescences are one of the distinctive characteristics of the plant.

Another distinctive characteristic of the plant is the deep vinous purplish color of the leaves in the summer months. This leaf color is far superior to other known varieties of Rhus Cotinus plant.

Further, the autumn coloring is considerably richer than that of prior varieties.

In the autumn, and particularly in September or when the cooler nights of fall have become settled, spots of mildew develop on the upper surfaces of the leaves. These spots, range from yellow, comparable to Plate 11–H–5, through Oakbuff, comparable to Plate 13–D–7, to a greenish yellow, comparable to Plate 14–K–1. This mildew on the leaves produces an unusual and very attractive pattern as the leaves ripen and constitutes a third distinctive characteristic of the plant.

Having shown and described a new variety of Rhus Cotinus plant, what is claimed is:

The new and distinct variety of Rhus Cotinus plant, substantially as herein described and illustrated.

No references cited.